United States Patent [19]
Mecikalski et al.

[11] Patent Number: 6,055,980
[45] Date of Patent: May 2, 2000

[54] DRY POWDER INHALER

[75] Inventors: Mark B. Mecikalski, Tucson, Ariz.; David R. Williams, San Diego; David O. Thueson, Poway, both of Calif.

[73] Assignee: Dura Pharmaceuticals, Inc., San Diego, Calif.

[21] Appl. No.: 09/120,549

[22] Filed: Jul. 22, 1998

Related U.S. Application Data

[63] Continuation of application No. 08/756,654, Dec. 26, 1996, abandoned, which is a continuation-in-part of application No. 07/702,194, May 20, 1991.

[51] Int. Cl.[7] .................................................. A61M 15/00
[52] U.S. Cl. .................. 128/203.15; 128/203.21
[58] Field of Search ......................... 128/203.12, 203.15, 128/203.21; 604/58

[56] References Cited

U.S. PATENT DOCUMENTS

| | | | |
|---|---|---|---|
| 3,831,606 | 8/1974 | Damani | 128/203.15 |
| 5,577,497 | 11/1996 | Mecikalski et al. | 128/203.15 |

*Primary Examiner*—Aaron J. Lewis
*Attorney, Agent, or Firm*—Lyon & Lyon LLP

[57] ABSTRACT

A dry powder medicine inhaler has an impeller non-concentrically disposed in a mixing chamber. A motor spins the impeller at high speed. A plunger introduces a dose of powdered medicine into the chamber so that all powder particles are available for intermixing disaggregation and comminution. An aperture receives a first stream of air and passes it towards the mouthpiece for inhalation by the user. A wall has at least one aperture for diverting a portion of a main air stream into the aerosolizing chamber to mix with the particles to form a fine, low-density, low velocity, dry mist of powdered medicine for inhalation by the user.

21 Claims, 11 Drawing Sheets

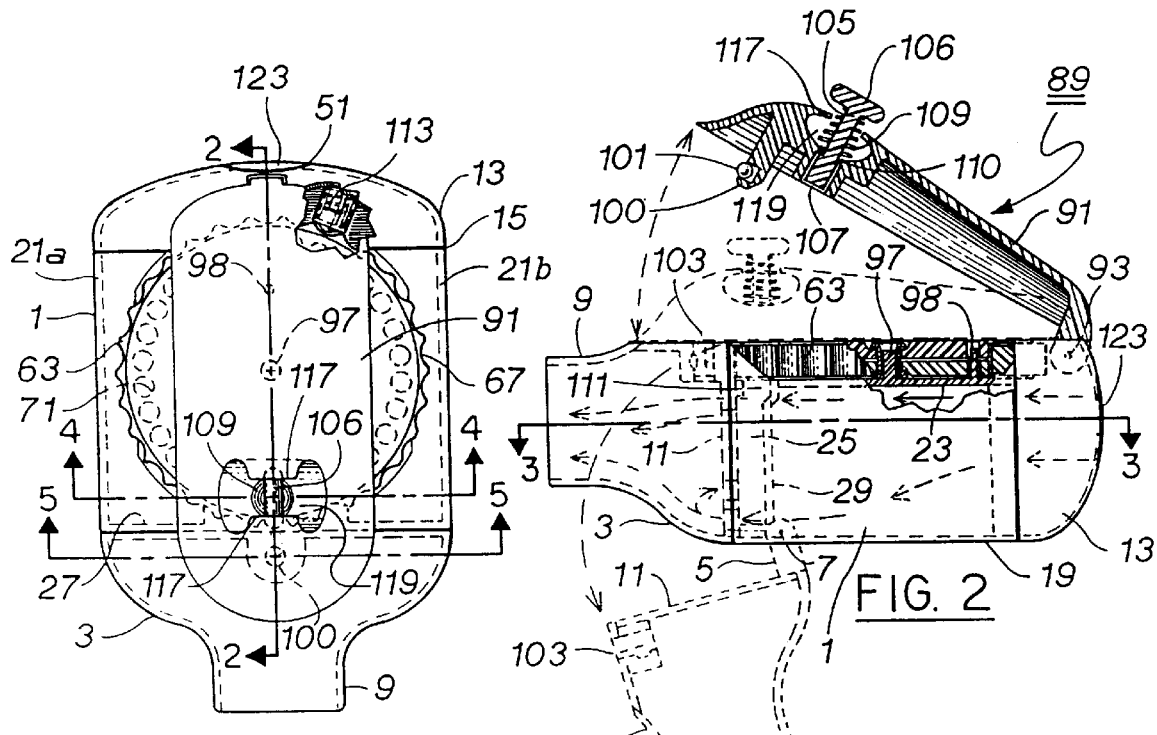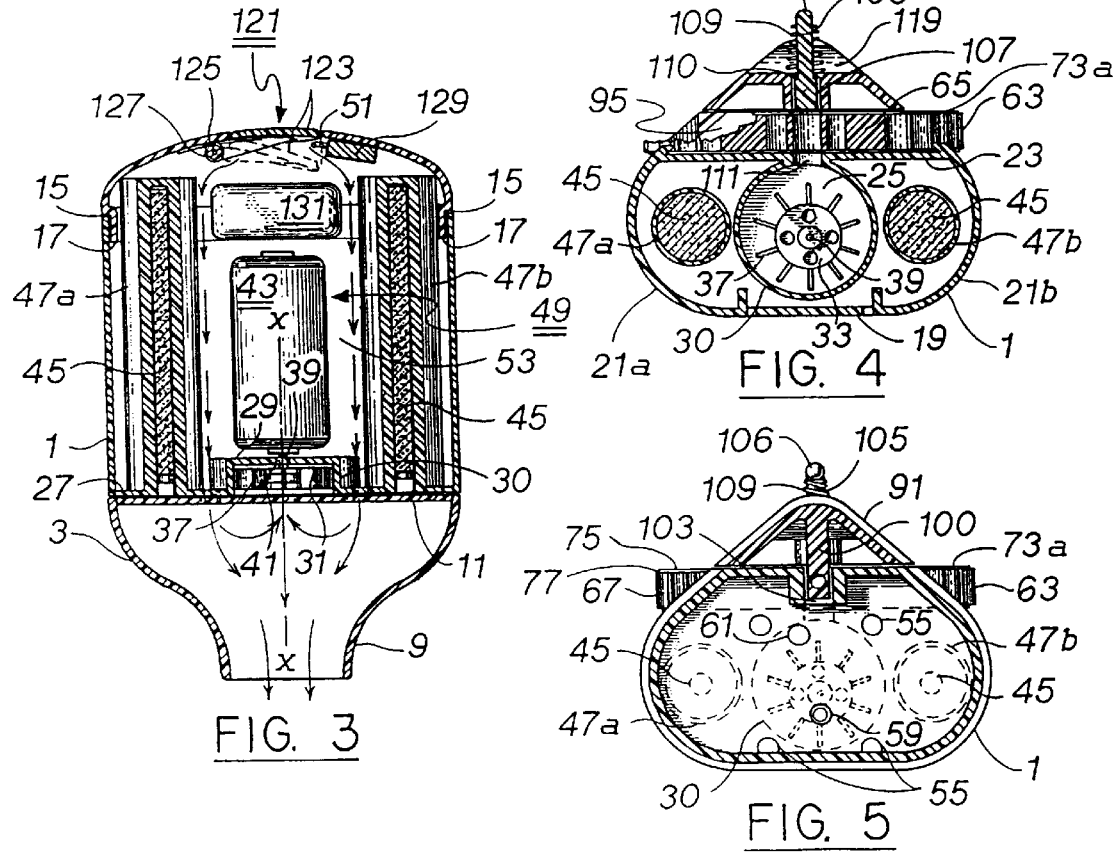

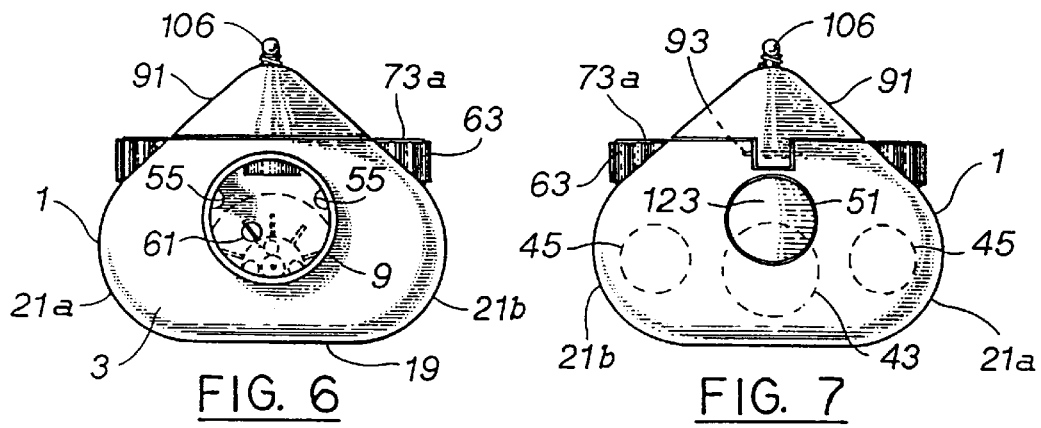
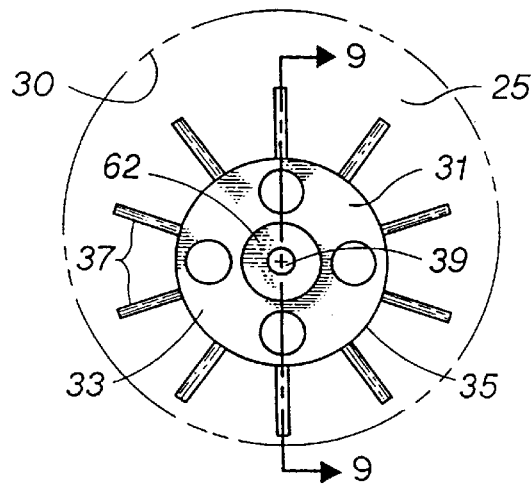
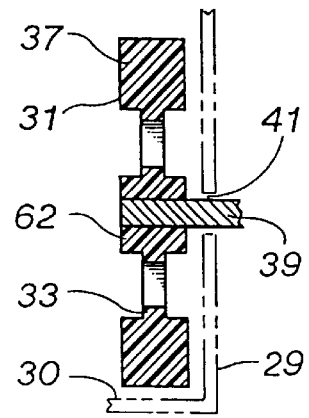
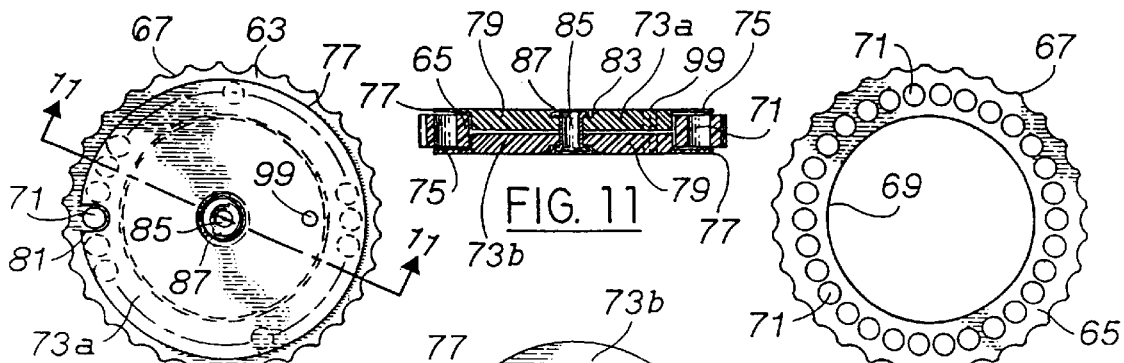
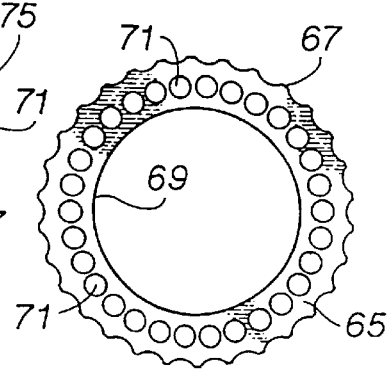
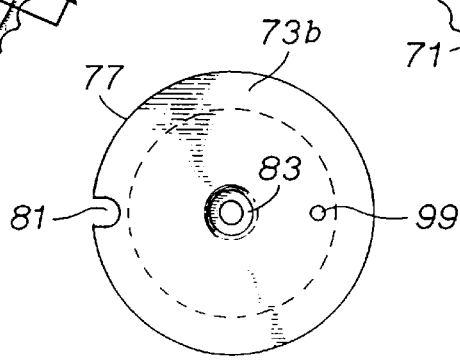

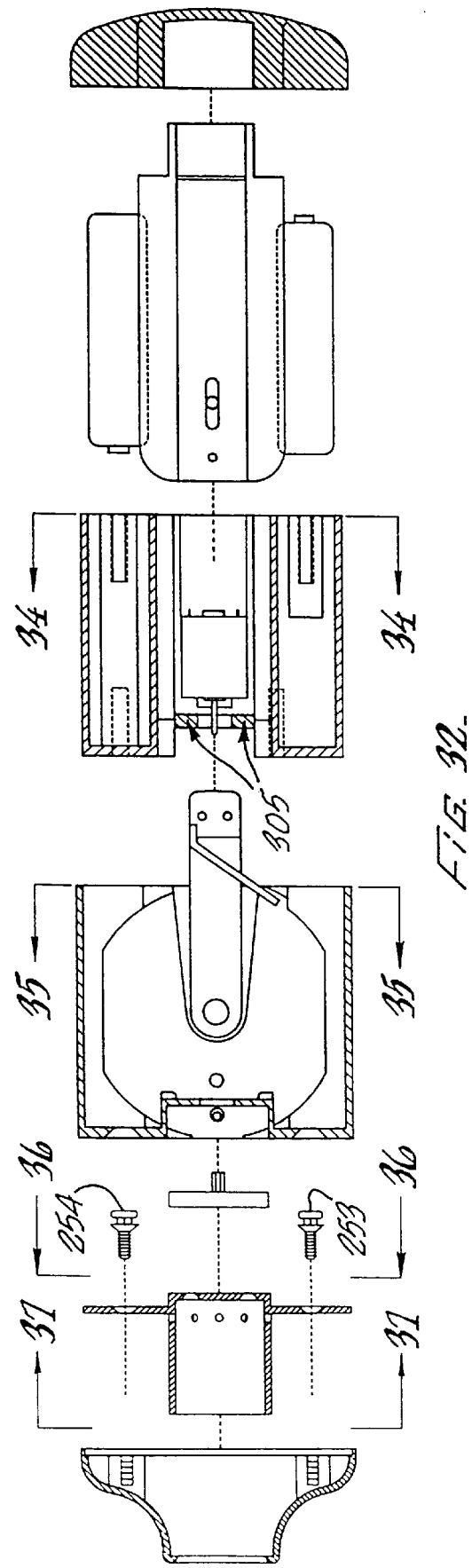

DRY POWDER INHALER

This is a continuation of application Ser. No. 08/756,654 filed Nov. 26, 1996 now abandoned and which in turn is a continuation-in-part of U.S. patent application Ser. No. 07/702,297 filed May 20, 1991.

BACKGROUND OF THE INVENTION

1. Field of the Invention

The field of the invention is inhalers for dry powder inhalants or drugs.

1. Description of the Prior Art

Beginning in the early 1970's, it was found that certain medicines could be administered in dry-powder form directly to the lungs by inhalation through the mouth or inspiration through the nose. This process allows the medicine to bypass the digestive system, and in some cases, allows smaller doses to be used to achieve the same desired results as orally ingested medicines. In other cases, it provides a delivery technique for medicines that display unacceptable side effects when taken by other methods.

Various devices or nebulizers that form inhalable mists of medicines are known in the art. They are divided between those that form mists of liquid medicines, those that form mists of powdered medicines, and those that may be used to form mists of both liquids and powders. The physical characteristics of powdered medicines, with particle sizes ranging from about 1 micron (0.001 mm) to about 100 microns, and more particularly from about 1 to about 5 microns, are significantly different from those of liquid medicines. There is little similarity between the engineering requirements and the physical designs of these two types of devices. Although some devices are intended to aerosolize both liquid and dry powder medicines, these devices would not appear to be highly efficient in operation.

Typical prior art devices for handling dry medicines are shown and described in U.S. Pat. Nos. 3,507,277; 3,518,992; 3,635,219; 3,831,606; 3,971,377; and 4,147,166. Several of these devices have been used, however, most of them have apparently not found wide acceptance. Most of these prior art devices use powdered medicine contained in a gelatin capsule with a separate dose contained in each capsule. These capsules are small and require significant manual dexterity to load and unload. A large portion of potential users of dry powdered medicines are found in the senior-citizen sector of the population and, unfortunately, this coincides with the major group of those inflicted with various forms of arthritis. With the minute size of the capsules and the requirements to load and unload them each time the nebulizer is used, they can be difficult to use.

Further, loading individual capsules with individual doses of powdered medicines can be time-consuming and thus makes the dosage in capsule a costly item. People who use a nebulizer during their daily routine are required to carry a large number of capsules which might leak thus lowering the effective dosage of the medicine.

Virtually all of these known devices involve the use of capsules that are pierced along their sides by needles or other sharp objects. Thereafter, the powdered medicine is slowly withdrawn from the capsules by either partial vacuum, caused by forced inspiration by the user, or by centrifugal force. Some of these devices require prolonged forced inspiration to extract the medicine. This requires the user to repeatedly inhale rather large volumes of air, each with a little dose of medicine, which can cause dizziness. In addition, all of the powder in the capsule may not be inhaled.

Water can pass through the walls of gelatin capsules. In high humidity areas, water vapor can penetrate the capsule and cake the medicine. If caked, it is extremely unlikely that all of the medicine would be inhaled from the capsule so that the dosage between capsules would vary, thus reducing the effect of the medicine.

Slow introduction of powdered medicine from the perforated capsule into the aerosolizing chamber, coupled with the airflow through the chamber, means that not all of the powder particles are present in the chamber at any one time. It has been found that self-scouring or inter-particle impact is an important feature in clearing the powdered medicine from the chamber for introduction into the lungs. Accordingly, dribbling the powdered medicine out of the capsule and into the chamber reduces the amount of self-scouring and allows cake buildup of the medicine in various parts of the chamber.

Another important factor is that it has not been realized that several important benefits are obtained if the delivery of a drug is relatively independent of the patient's inspiratory flow rate (i.e., how deeply the patent inhales) or coordination (i.e., the patient's timing of the inhalation). An inspiratory flow rate independent device can be used by patients with low inspiratory flow rates, such as children or patients experiencing aspiratory distress. Moreover, if the delivery of a drug is independent of the patient's inspiratory flow rate, the inhaled dosage will remain relatively consistent regardless of the patient's inhalation characteristics. Metered dose inhalers, typically using a propellant gas, require significant coordination for proper use. Actuation must occur during inspiration, or the majority of the drug will be deposited in the throat. It is now appreciated that a breath-actuated device will minimize the need for patient coordination.

Whether or not to allow the user to exhale into the device can be an important factor. The perforated capsules admit medicine very slowly into the inhalating airstream. In addition, many users are elderly persons or those who suffer from lung disease. These two factors may combine to render the user incapable of inhaling all of the medicine in one breath. Therefore, it is important to consider the possibility that the user will exhale into the device. Exhaling involves a high-humidity airstream. When it enters the device, it may cause some moisture condensation on the interior walls. In other cases, moisture-laden air may be blown into the aerosolizing chamber causing the powdered medicine to cake and fail to be extracted by later inhalations. Consequently, repeated exhaling into a device and its potential for caking of powdered medicine remains a significant disadvantage.

Moreover, the beneficial effects of reducing the size of large particles or agglomerated particles during use of the device have apparently not been appreciated previously. Large or agglomerated particles of medicine gather momentum during forced inhalation or inspiration and impact the soft, wet tissue surrounding the throat and larynx instead of remaining in the air flow for deposit in the lungs. When this occurs, much of the medicine apparently does not reach deep into the interior of the lungs and thus is not placed in a strategic location where it will be solvated for direct absorption through the areolar tissue into the blood stream. In more severe cases, such impact may cause coughing and thus could force large volumes of moisture-laden air, as well as finely dispersed saliva, to be reinjected into the device leading to caking of the medicine.

Accordingly, it is an object of the invention to provide an improved dry powder inhaler.

SUMMARY OF THE INVENTION

To these ends an inhaler has a chamber for mixing air and a powdered drug or inhalant. Air flows into the chamber and is mixed with the powdered inhalant via an impeller spinning within the chamber. The drug-laden air flows out of the chamber and into a mouthpiece. Preferably, outside air also flows into the mouthpiece around the drug-laden air. The inhaler is substantially flow rate independent. Preferably, the devise uses breath-actuation and is generally independent of patient coordination. Doses of a drug may be dispensed from a multiple-dose cartridge mounted on the inhaler into the chamber. The rate of air flow through the chamber and the rotation speed of the impeller can be adjusted for different drugs for increased delivery efficiency.

BRIEF DESCRIPTION OF THE DRAWINGS

Other objects and features of the present invention will become apparent from the following detailed description taken together with the accompanying drawings which disclose two embodiments of the invention. The drawings, however, are provided for illustration purposes only and are not intended as a limitation on the scope of the invention.

In the drawings, wherein similar reference characters denote similar elements through the several views:

FIG. 1 is a top plan view of a preferred embodiment of the invention;

FIG. 2 is a side elevational view of the embodiment shown in FIG. 1 with the dosage injector handle lifted out of its secured, traveling position and the front piece rotated downward to expose the interior of the device;

FIG. 3 is a top sectional view of the preferred embodiment taken along lines 3—3 in FIG. 2;

FIG. 4 is a front sectional view taken along lines 4—4 in FIG. 3 showing the aerosolizing chamber and the impeller in nonconcentric relationship;

FIG. 5 is another front sectional view taken along lines 5—5 in FIG. 3 forward of the rear wall of the front mouth piece showing the preferred position of the air inlet holes;

FIG. 6 is a front end view of the embodiment shown in FIG. 1;

FIG. 7 is a rear end view of the embodiment shown in FIG. 1;

FIG. 8 is a closeup view of the aerosolizing chamber showing the position of the impeller in non-concentric relationship therein;

FIG. 9 is a side elevational sectional view of the impeller shown in FIG. 8;

FIG. 10 is a top plan view of the assembled dose cartridge usable in the embodiment shown in FIG. 1;

FIG. 11 is a sectional side view of the dose cartridge taken along lines 11—11 in FIG. 10;

FIG. 12 is a top view of the ring portion of the cartridge showing the apertures for holding the doses of medicine;

FIG. 13 is a top view of one of the cover plates shown in FIG. 10;

FIG. 27 is a side elevation view of the ring portion of FIG. 25;

FIG. 32 is a top elevation exploded view of the inhaler of FIG. 14;

DESCRIPTION OF THE PREFERRED EMBODIMENTS

Figure 14:
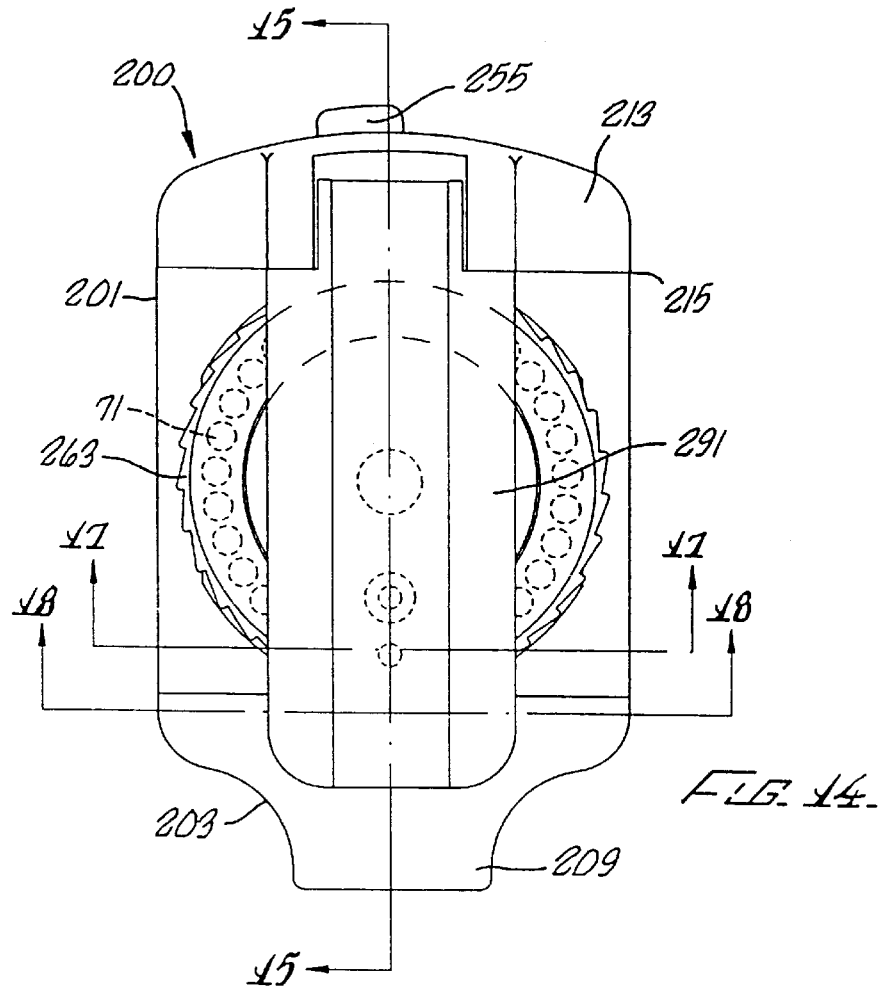
FIG. 14 is a top plan view of a second preferred embodiment of the invention.

FIGS. 1–3 show the overall view of the first preferred embodiment where a hollow front end piece 3 is pivotally mounted onto an inner central core 1 by a pair of tabs 5. A pair of pins 7 have ends mounted in core 1 for pivoting piece 3 outward and downward from core 1. The front end piece 3 includes a hollow tubular mouth or nose piece 9 formed at the front and a rear wall 11 closing off the rear of piece 3. A back end piece 13 is attached to the core 1 about a marginal edge 15 by a snap skirt 17 or other known connection. Core 1 conveniently has a flattened bottom 19, a pair of spaced apart rounded sidewalls 21a and 21b and a flattened disk surface 23 for easy grasp by the user.

As shown in FIGS. 2, 3, 4 and 8, a disk-shaped or circularly-shaped aerosolizing chamber 25 is formed in the front wall 27 of core 1 transversely to the air flow, shown by the arrows in FIGS. 2 and 3 existing mouthpiece 9. Chamber 25 is preferably on the order of one-half inch in diameter and one-eighth inch thick, and the ratio of the chamber diameter to chamber thickness (or depth) is preferably approximately 4:1. Chamber 25 is bounded at the front by a portion of the rear closure wall 11, at the back by a smooth wall 29 and about the periphery by a circumferential wall 30.

An impeller 31, shown in FIGS. 3, 4, 8 and 9 comprises a thin, flat circular plate 33, having a peripheral edge 35. A plurality of short blades 37 extend radially outwardly from the peripheral edge 35. The plate 33 is positioned non-concentric or off-center within the chamber 25. As shown in FIGS. 4 and 5, the impeller 31 is positioned below the geometric center of aerosolizing chamber 25 toward the lower part of circumferential wall 30. The front surface of the impeller is very close to the rear wall 11. The impeller 31 is mounted on a central shaft 39 that extends through a hole 41 formed in rear chamber wall 39 and arranged for high-speed power rotation about a fixed axis x—x as shown in FIG. 3. Shaft 39 is connected to a high-speed electric motor 43 that is driven by at least one, but preferably a pair of batteries 45. The batteries 45 are carried in space-apart bores 47a and 47b. The aerosolizing chamber 25 is opened and exposed for maintenance of cleaning by pivoting the front end piece 3 about pins 7 as shown in FIG. 2.

A plenum or flow path 49 as shown in FIGS. 3, 5 and 7, passes a first throttled stream of air through inner core 1 toward mouthpiece 9 for inhalation by the user. The flow path 49 includes at least one opening 51 formed in back end piece 13 for receiving outside air into core 1. Passage ways 53 are formed through the inner core 1, in communication with opening 51, to allow passage of the airstream, shown by arrows in FIGS. 2 and 3, through core 1 toward mouthpiece 9. The passageways lead into hollow front end piece 3 through at least one but preferably a plurality of throttling apertures 55 formed in rear closure wall 11, as shown in FIG. 5. The size of aperture 51, passage ways 53, and apertures 55 are set to provide significant resistance to air flow, to throttle the velocity of said airstream through core 1 and into the user's mouth. This apparently reduces particulate momentum and hence impaction against the rear of the user's throat.

A portion of the main stream of air is diverted, as shown by the arrows in FIGS. 2 and 3, for sweeping through aerosolizing chamber 25 and carrying the powdered medicine back into the main stream of air. This is accomplished by providing an inlet aperture 59 formed in the rear closure wall 11 near the center of the impeller 31. An outlet aperture 61 is formed in the rear closure wall 11 at the top of aerosolizing chamber 25. As the motor 43 drives the impeller 31 at a high speed, the impeller acts as a centrifugal air pump drawing air in through the inlet aperture 59, mixing the air with the full dose of powdered medicine inside chamber 25 and expelling the air and medicine as a fine, low-density dry mist out through the outlet aperture 62. This powder-laden air or mist then combines with the main throttled stream of air in the mouthpiece 9 for inhalation by the user. Apertures 59 and 61 are sized such that the mist emerges from chamber 25 through aperture 61 at a clinically negligible velocity. The size of inlet aperture 59 may be set, for example, at 0.093 inches in diameter and the size of outlet aperture 61 may be set, for example, at 0.062 inches in diameter. This low velocity combines with the first throttled airstream to produce a fine, low-density dry mist that is easily inhaled by the user without forced inhalation. Because there is no longer the piercing of a capsule or use of vacuum or centrifugal force to remove the medicine from the capsule, users need no longer strain to suck the medicine into their lungs.

The impeller 31 is rotated by the electric motor 43 at extremely high speed such as 12,500 rpm. Such a high speed causes a high velocity flow and turbulence of the powder in the air stream and, with the unbalancing of this flow, resulting from the offset of impeller 31, causes the particles to impact each other and chamber walls 11, 29 and 30 to comminute and disaggregate them into smaller, more respirable-size particles. This effect further causes the particles to become intimately mixed with the air flow to provide a self-cleaning action on the walls of the chamber. Because of the offset location of impeller 31 in chamber 25, the high velocity circulation of air is at different pressures and velocities at different points about chamber 25. This effect appears to promote turbulent mixing of the particles and air and reduces caking of the powdered medicine. As shown in FIG. 5, inlet aperture 59 can be placed over a wide area below impeller boss 62 but preferably it is just below boss 62 and above paddles 37 to provide a less restricted entrance into chamber 25. Similarly, outlet aperture 62 may be located virtually anywhere above impeller boss 62 but it is preferred to locate it above paddles 37 and on one side or the other of the centerline of chamber 25. Should the user attempt to draw or suck air in through mouthpiece 9 at a high rate, a partial vacuum will be created in inner core 1, however this vacuum would exist over the total internal volume of inner core 1 so that the centrifugal pumping action of offset impeller 31 would be unaffected by the vacuum or by the degree to which the user draws or sucks on mouthpiece 5.

A multi-dosage medicine containing cartridge 63 is shown in FIGS. 10–12 for use in the embodiment of FIG. 1. As shown in FIG. 12, cartridge 63 comprises a relatively thin ring 65 of plastic or other lightweight material having a scalloped outer edge 67 and a smooth inner edge 69. A series of apertures 71 are formed through ring 65 between outer edge 67 and inner edge 69 receive and hold doses of powdered medicine. A pair of cover plates 73a and 73b having a thin outer flange 75 and outer edge 77 and a thicker inner portion 79 are provided to cover both sides of ring 65 as shown in FIGS. 10 and 11. A U-shaped opening 81 is formed in the flange 75 of each cover plate. The plates placed in faced-together arrangement, as shown in FIG. 11, to sandwich ring 65 therebetween. The outer edge 77 is sized to terminate short of scalloped outer edge 67 of the ring as shown in FIG. 10. U-shaped openings 81 in cover plates 73a and 73b are aligned one above the other as shown in FIG. 10 so that the dose of medicine contained in each aperture is exposed, one at a time, as ring 65 is rotated between cover plate 73a and 73b. A center depression 83 is formed in cover plates 73a and 73b adjacent a center bore 85. A hollow rivet 87 or other fastening device is installed in the bore to hold cover plates 73a and 73b together over ring 65.

A mounting mechanism 89 is provided for mounting dosage cartridge 63 onto the inner core 1 and for introducing medicine into aerosolizing chamber 25. The mounting mechanism 89, as shown in FIGS. 1 and 2, includes a hold-down lever 91 pivoted by a pin 93 mounted in back end piece 13. An open area 95 is formed in core top surface 23 for receipt of dosage cartridge 63 on a center peg 97. An offset peg 98 extends into a small aperture 99 formed through plates 73a and 73b to immobilize cover plates 73a and 73b. A fastening post 100 containing a spring loaded ball catch 101 extends from the front end of hold down lever 91 and is adapted for insertion into a receiving bore 103 formed in the upper rear portion of front end piece 3.

A medicine-charging plunger 105, with a T-shaped top bar 106, is reciprocally mounted in a bore 107 in hold-down lever 91 and biased upward by a spring 109 against a stop 110 formed in plunger 105. A medicine-charging chute 111 is formed in inner core 1 below plunger 105 and extends down into the top of aerosolizing chamber 25. Preferably, the diameter of chute 111 matches the diameter of aperture 71.

In use, dosage cartridge 63 is placed on pegs 97 and 98 in open area 95. Hold-down lever 91 is pivoted downwardly to retain the cartridge and lock mouthpiece 9 in its operable closed position. U-shaped openings 81 in cover plate 73a and 73b are automatically aligned below medicine-charging plunger 105 by the arrangement of aperture 99 and offset peg 98. Aerosolizing chamber outlet 61 is preferably offset from just below chute 111 to prevent interference with the charging of medicine or with having outlet 61 becoming jammed with medicine during charging.

A spring-loaded ball 113, shown in FIG. 1, is formed in rear end piece 13 so that said ball is biased against a scalloped outer edge 67 to prevent unwanted movement of dosage cartridge ring 65. Ring 65 is then rotated to bring a medicine filled aperture 71 into alignment over the chute 111. The charging plunger 105 is pressed downwardly against the bias from spring 109 to press the full dose of powdered medicine directly into aerosolizing chamber 25. Thereafter, plunger 105 remains in the chute 111 to form the top portion of circumferential wall 30 of aerosolizing chamber 25. The plunger 105 may be held there, against spring bias by turning the plunger handle 106 under overlying leaves 117 spaced about a hollow area 119 formed in the front part of hold down lever 91, as shown in FIG. 1.

An exhalation exclusion system 121 is provided for preventing exhalation by the user into the apparatus so that no breath moisture is available to cake the powder. The exclusion system 121 includes a one-way valve 123 or flapper hingedly mounted by pin 125 interior of aperture 51 in back end piece 13. A spring 127 is connected to flapper 123 to bias it into a closed position over aperture 51 during all handling of the apparatus other than when the user is drawing air in through mouthpiece 9. When the user inhales or draws air in through inner core 1, the reduction of internal pressure in core 1 allows atmospheric pressure on flapper 123 to overcome the bias of spring 127 and force it to open to admit air into inner core 1 to create the first stream of air as previously described. A normally-opened electric switch 129 is connected to flapper 123 and interconnected between electric motor 43 and batteries 45 through an electric box 131, formed in core 1, to insure that motor 43 is not energized by batteries 45 unless flapper 123 is opened. Flapper 123 will open when the user draws air in through mouthpiece 9 to inhale the aerosolized powdered medicine.

The volume of many medicines, in their dosage amounts, is often extremely small. It has been a practice for many years to dilute these small volumes with inert filler materials to increase the overall volume to handleable sizes, as in aspirin tablets and the like. So too, in the field of inhalable powder medicines there has been an established practice of adding inert powders to the medicine to bring the volume up to a size that can be efficiently inhaled.

However, apparently little or no attention has been paid to the size of particles of inert powder vis-a-vis the problem with large particle momentum and cake buildup. It has now been discovered that mixing a quantity of carefully sized, substantially larger particle inert powder with virtually any dosage of fine active ingredient or medicine powder will provide a useful mixture of particle sizes that will intermix or undergo comminution and self-scouring in the aerosolizing chamber. With this mixture, the powder is disaggregated and comminuted into small sized particles able to be swept out of the aerosolizing chamber first, while the larger particles of inert material act to scour and clean the internal surfaces of the aerosolizing chamber. The larger particles thereafter undergo self-comminution and self-scouring for inhalation by the user. Because of the low velocity of air coming through the mouthpiece by virtue of the throttling action of the flow path 49, there apparently is generally insufficient momentum given to any large particles to cause impaction with the soft moist tissue of the throat and larynx. Accordingly, by providing a diluent in the form of particles of nontoxic substances, such as lactose, where a substantial amount of them are in the size range of 50 micron diameter particles and higher, the medicine, having a small particle size, is cleared out of the aerosolizing chamber, notwithstanding initial humidity in the medicine.

Figure 15:
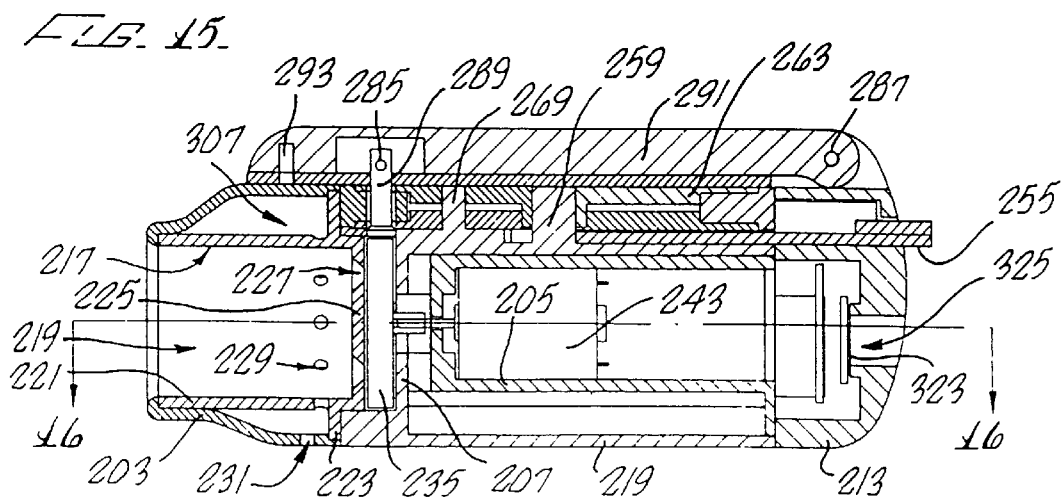
FIG. 15 is a section view taken along line 15—15 of FIG. 14.

A second embodiment 200 of the present inhaler is shown in FIGS. 14–37. Referring to FIGS. 14 and 15, the inhaler 200 has a core or housing 201. A front end piece 203 at the front of the housing 201 tapers to a mouthpiece 209 having a diameter comfortably accommodated by the user's mouth. The housing 201 has a flat bottom surface 211. A back end piece 213 is attached to the rear of the housing 201. A powdered medicine cartridge 263 is pivotally supported on top of the housing 201, with a hold down lever 291 overlying the cartridge 263.

Referring to FIG. 15, a front cylinder 217 has cylindrical walls 221 and a back plate 225 which form a front chamber 219. A flange 223 extends radially outwardly from the cylindrical walls 221 just forward of the back plate 225. Countersunk outflow holes 227 pass through the back plate 225 with a feather edge or sharp edge at the rear surface of the back plate. The outflow holes 227 are preferably provided in the pattern shown in FIG. 37. Radial holes 229 extend through the cylindrical walls 221 of the front cylinder 217 into the front chamber 219 just forward of the outflow holes 227. Preferably, the radial holes 229 are provided equally spaced apart on the cylinder walls 221. A powder chute 261 extends through the top surface of the housing 201 into the impeller chamber 235. A front air inlet 231 extends through the front end piece 203 into a distribution chamber 307 formed in between the front end piece 203 and the front cylinder 217.

Figure 16:
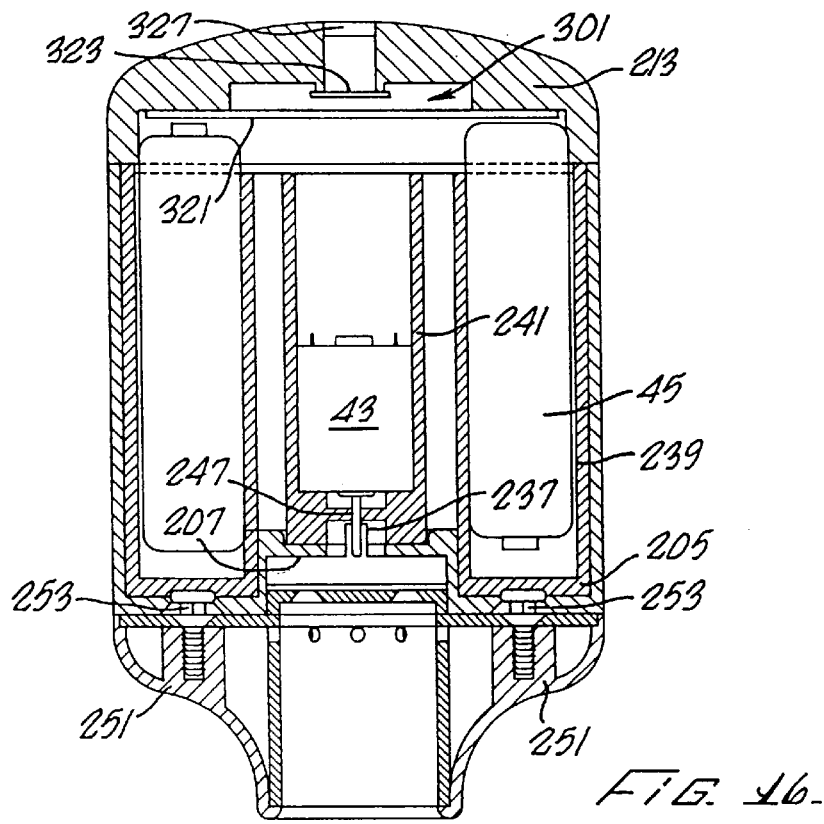
FIG. 16 is a section view taken along line 16—16 of FIG. 15.
Figure 17:
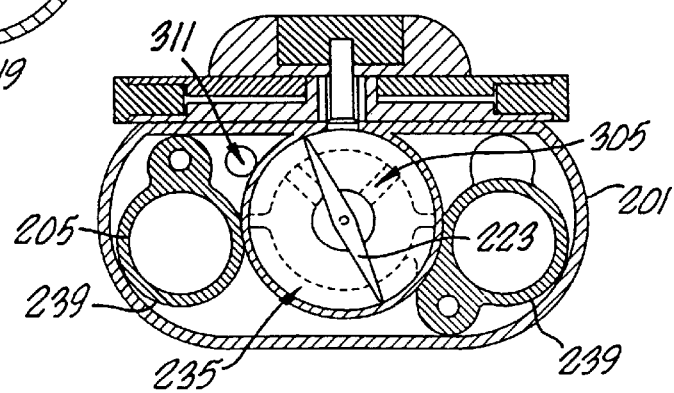
FIG. 17 is a section view taken along line 17—17 of FIG. 14.
Figure 19:
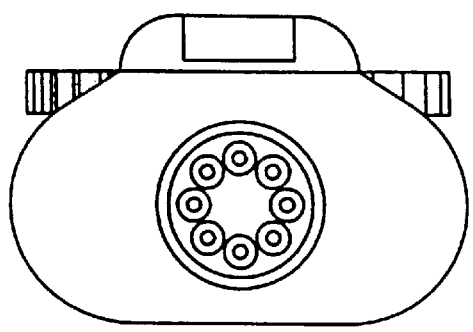
FIG. 19 is a front end view of the embodiment shown in FIG. 14.
Figure 20:
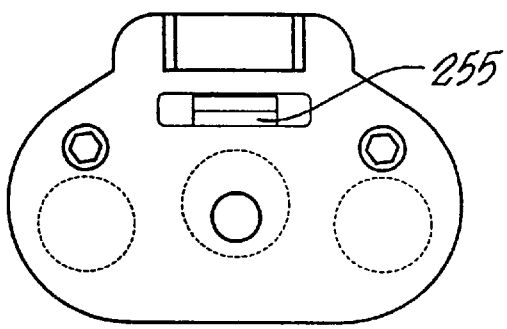
FIG. 20 is a rear end view of the embodiment shown in FIG. 14.
Figure 33:
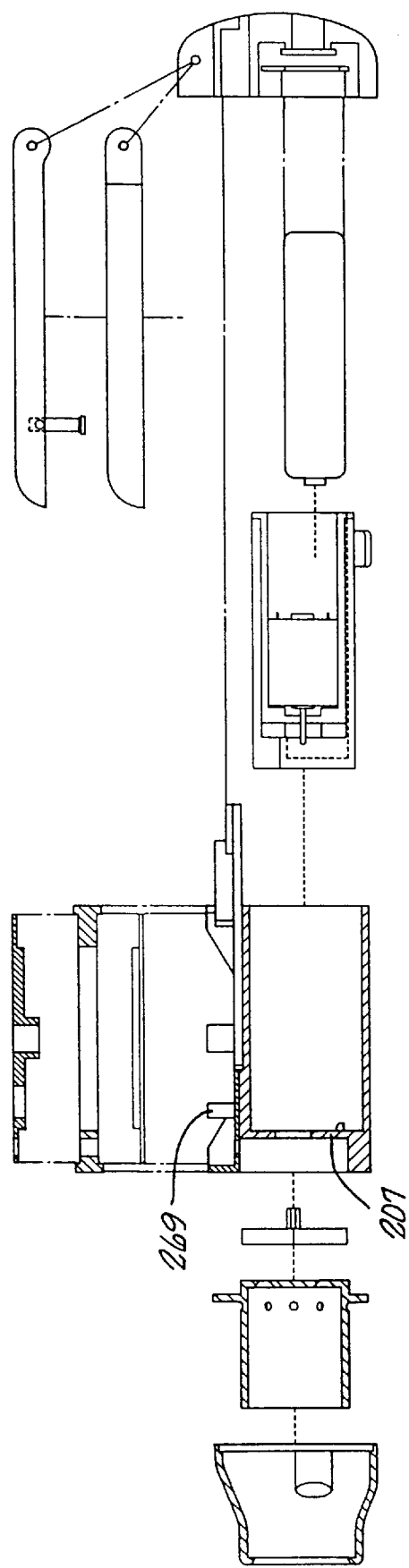
FIG. 33 is a side elevation view thereof, in part section.
Figure 34:
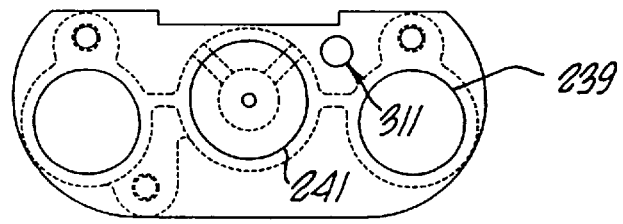
FIG. 34 is an end view of the motor chassis, taken along line 34—34 of FIG. 32.
Figure 35:
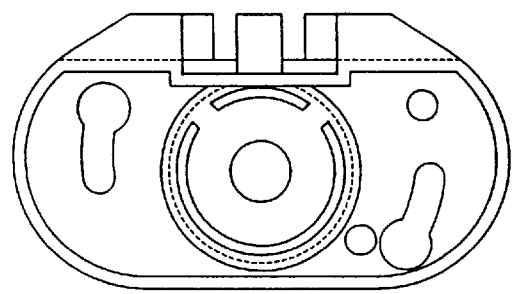
FIG. 35 is an end view of the housing taken along line 35—35 of FIG. 32.
Figure 36:
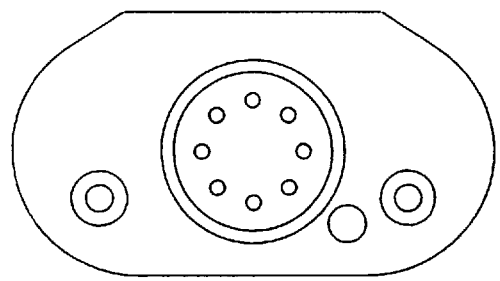
FIG. 36 is a rear end view of the front cylinder taken along line 36—36 of FIG. 32.
Figure 37:
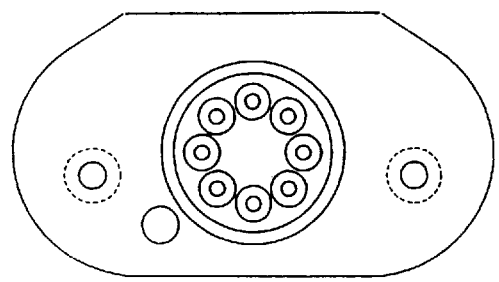
FIG. 37 is a front end view thereof taken along line 37—37 of FIG. 32.

Referring to FIGS. 15, 16 and 17, a motor chassis 205 is secured within the housing 201. The motor chassis 205 has two side battery tubes 239 linked to a central motor tube 241 by webs 245, as shown in FIGS. 32–34. A partition wall 309 having an air supply hole 311 extends across the back end of the motor chassis 205.

Figure 21:
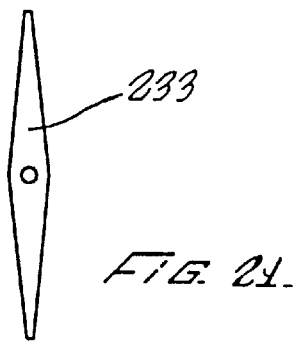
FIG. 21 is an enlarged front elevation view of the impeller of the embodiment of FIG. 14.
Figure 22:
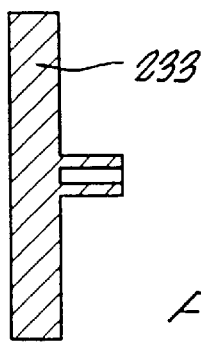
FIG. 22 is a section view taken along line 22—22 of FIG. 21.

A high speed miniature electric motor 243 is contained within the forward end of the motor tube 241, as shown in FIG. 16. A motor shaft 237 extends from the motor 243 through a shaft opening in the front wall 247 of the motor tube 241, and into an impeller chamber 235. An impeller 233 is attached to the motor shaft 237 for rotation within the impeller chamber 235. As shown in FIGS. 21 and 22, the impeller 233 has two oppositely extending tapering arms forming an equilateral parallelogram.

The impeller chamber 235 is formed by a front wall 207 of the housing 201, a front rim 208 of the housing around the front wall 207, and by the back plate 225 of the front cylinder 217, although other configurations are available. The impeller chamber 235, as shown in FIGS. 15 and 16, is generally a disk-shaped open space. The impeller 233 fits within the impeller chamber 235 with a minimum clearance (preferably about 0.008–0.012 inches) both front to back, i.e., between the back plate 225 and the front wall 207 of the housing, and also radially with the length or diameter of the impeller 233 only slightly less than the diameter of the rim 208. This relatively close fit of the impeller within the chamber provides proper mixing interaction of the air and powdered drug. In contrast to the first embodiment, the impeller 233 is centered in the chamber 235.

Figure 18:
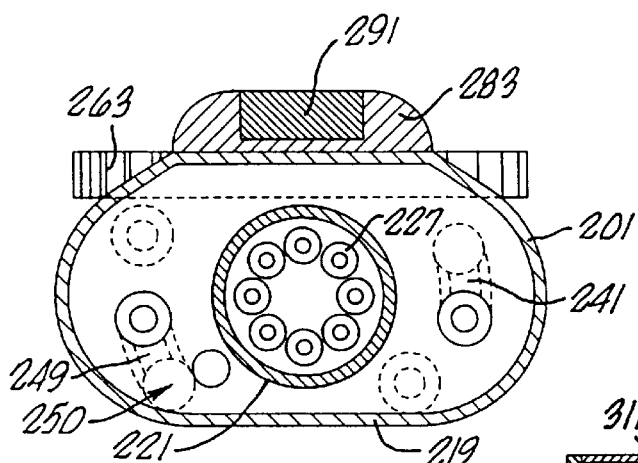
FIG. 18 is a section view taken along line 18—18 of FIG. 14.

Referring to FIGS. 16 and 32, the front end piece 203 has threaded bosses 251 on either side of the mouthpiece 209. The front cylinder 217 is attached to the front end piece 203 by screws 253 extending through holes in the flange 223 and threading into the bosses 251. The screws 253 have shoulder caps 254 which extend into mounting slots 249 in the housing 201, as shown in FIG. 18. The front end piece 203 and the front cylinder 217 can be attached to the housing 201 by inserting the shoulder caps 254 through slot holes 250 in the slots 249 and rotating the front end piece 203 through an acute angle. With the reverse sequence, these pieces can be removed to access the impeller chamber 235.

Figure 26:
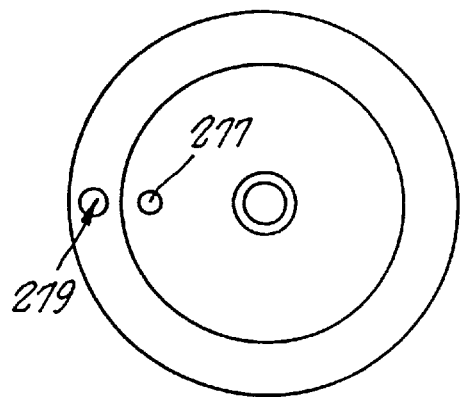
FIG. 26 is a top plan view of the cartridge assembly of FIG. 23 including a top cover plate.
Figure 25:
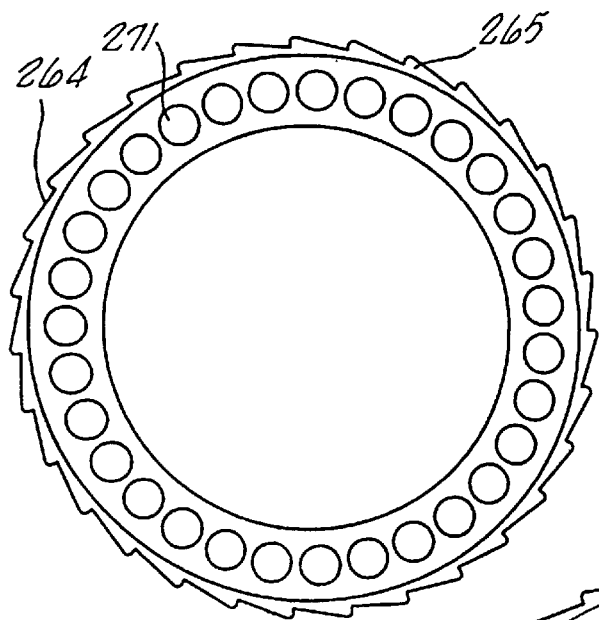
FIG. 25 is a top plan view of the ring portion of the cartridge of FIG. 23 showing the apertures for holding doses of dry powder.
Figure 23:
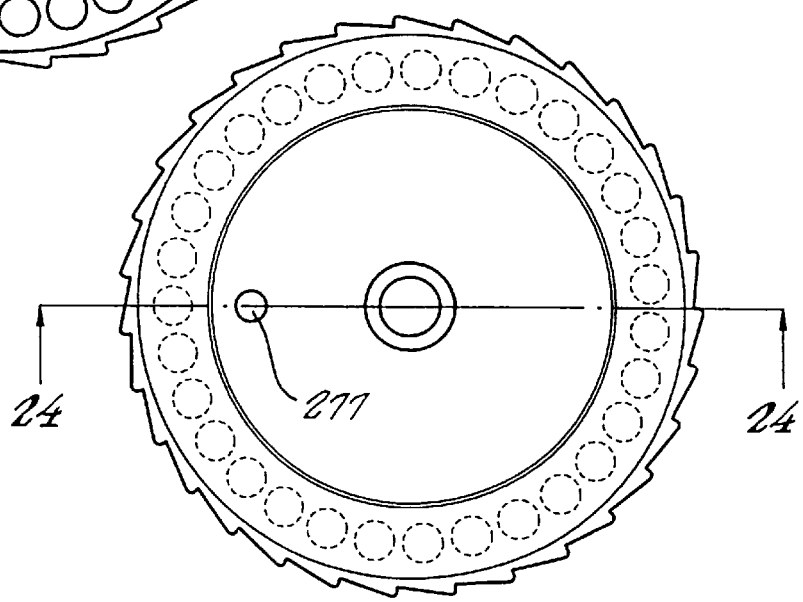
FIG. 23 is a top plan view of the assembled dose cartridge for use with the embodiment of FIG. 14.
Figure 22:
Figure 24:
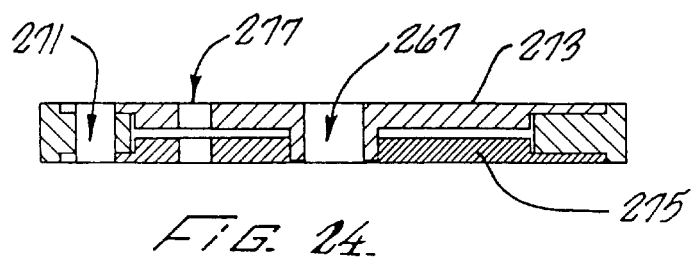
FIG. 24 is a section view taken along line 24—24 of FIG. 23.

The cartridge 263 supported on top of the housing 201 includes a cartridge ring 264 having sawtooth ridges 265, as shown in FIG. 25. Holes or apertures 271 extending longitudinally through the cartridge ring 264 are loaded (e.g., at factory or pharmacy) with dry powder medication. A top plate 273 and a bottom plate 275 are attached over and under the cartridge ring 264, to form the complete cartridge 263 and to prevent leakage or contamination of the powder in the apertures 271, as shown in FIGS. 23, 24 and 26. A rivet or other fastener or joint secures the top and bottom plate over the cartridge ring 264. Anti-rotation alignment holes 277 extend through the top and bottom plates 273 and 275. A chute hole 279 in the top plate 273 and bottom plate 275 is provided so that the apertures 271 can be accessed when brought into alignment with the chute 279.

Figure 28:
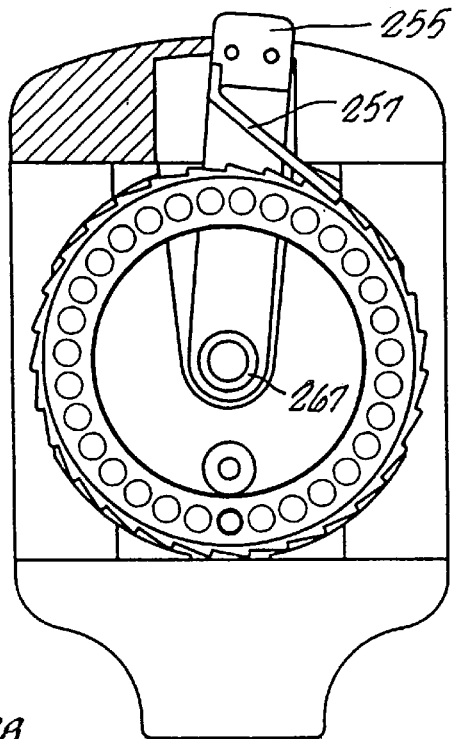
FIG. 28 is a top plan view of the inhaler of FIG. 14 with the hold down lever flipped up or removed and the cover plates on the cartridge removed, for illustration purposes only.

As shown in FIGS. 14, 15, 28 and 29, the cartridge 263 is placed on the housing 201 with a spindle 259 extending upwardly from the housing into the center hole 267 of the cartridge 263. A peg 269 also extending upwardly from the housing 201 passes through the peg holes 277 in the top plate 273 and bottom plate 275, to prevent the plates from turning with the cartridge ring 264. Referring to FIG. 28, a ratchet spring 257 on a ratchet support 255 on the housing 201 engages the ridges 265 around the perimeter edge of the cartridge ring 264, such that the cartridge ring can only be turned in one direction (i.e., clockwise as viewed in FIG. 28).

A lever frame 283 is pivotally attached to the back end piece 213 by a pivot pin 287. A snap 293 releasably secures the front of the lever frame 283 to the front end piece. A hold down lever 291 which nests within the lever frame 283 is also pivotally supported on pin 287. A piston 289 is pivotally attached to the hold down lever 291 by a pin 285. The piston 289 is aligned-with the powder chute 261.

Figure 31:
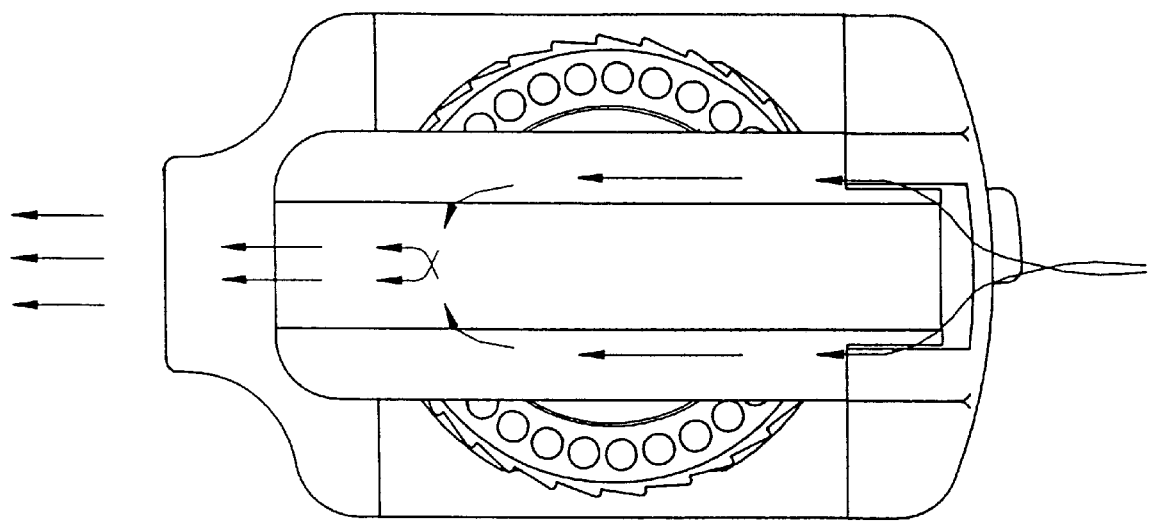
FIG. 31 is a top elevation view thereof.
Figure 30:
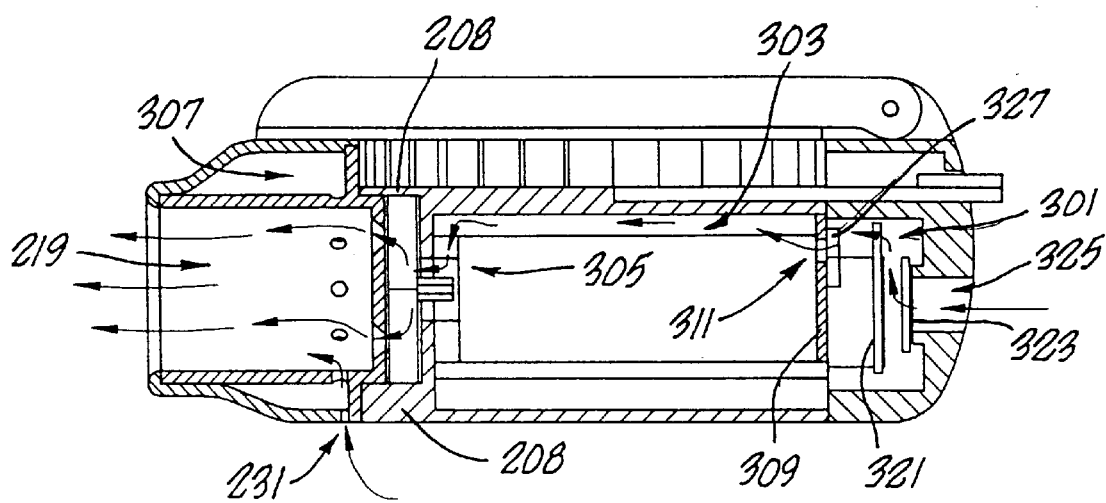
FIG. 30 is a side elevation view, in part section, of the inhaler of FIG. 14 schematically illustrating air flow paths therethrough.

Referring to FIGS. 30 and 31, an inflow port 325 extends through the back end piece 213. A one way valve 323 separates the inflow port 325 from a rear plenum 308 in the back end piece 213. An interconnect circuit board 321 extends across the rear end piece 213. The rear plenum 301 opens into a center plenum 303 through the air supply hole 311 extending through the partition wall 309. The center plenum 303 leads forward within the housing 201 to two channel slots 305 on the front wall 207 which lead into the impeller chamber 235. A switch 329 on the one way valve 323 is electrically linked to the motor 43 and batteries 45 through the circuit board 321 to switch the motor on when the one way valve opens.

Figure 29:
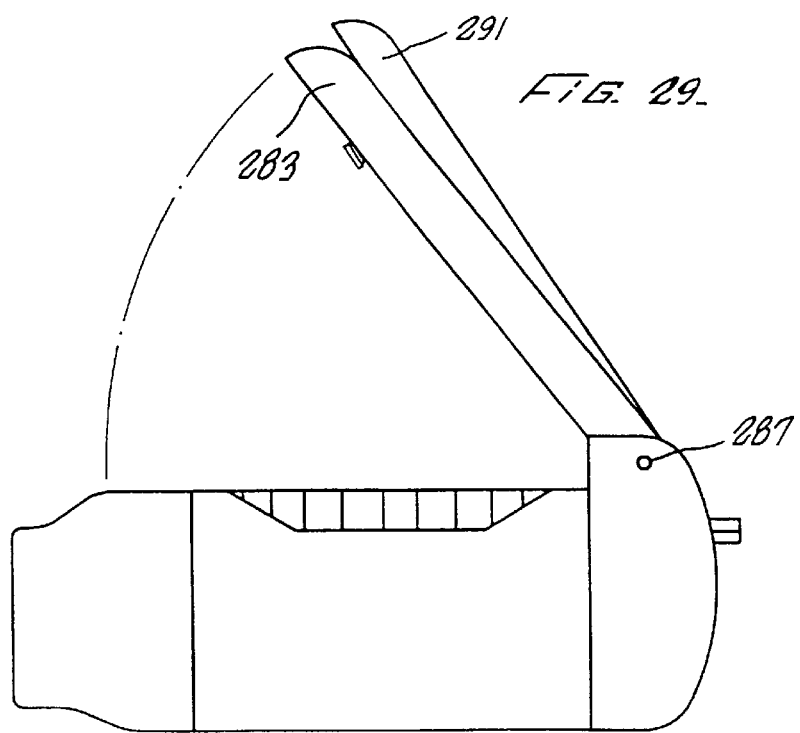
FIG. 29 is a side elevation view of the inhaler of FIG. 14 showing movement of the hold down lever.

In use, a cartridge 263 is loaded onto the inhaler 200 by pivoting the lever frame 283 and hold down lever 291 upwardly, as shown in FIG. 29. The cartridge 263 is installed on the spindle 259 with the peg 269 passing through the peg holes 277 in the top and bottom plates of the cartridge 263. The lever frame 283 is pivoted back onto the housing 201, and the hold down lever 291 is pivoted down with the piston 289 aligned with an aperture 271 in the cartridge 263. As the hold down lever 291 is pressed down, the piston 289 pushes the powder medication out of the aperture 271, through the chute 261 and into the impeller chamber 235. The piston 289 is dimensioned to closely match the diameter of the apertures 271, to drive virtually all powder out of the aperture. The piston 289 also extends fully through the chute 261, so that the full dose from the aperture is pushed entirely into the impeller chamber, with virtually no powder remaining in the chute 261. The volume of the dosage is very small compared to the volume of the impeller chamber, as shown in the drawings. The inhaler 200 is then ready for use.

The mouthpiece 209 is placed into the user's mouth. As the user gently inhales, a slight pressure drop is created in the front chamber 219, and correspondingly in the impeller chamber 235, the center plenum 303 and the rear plenum 301, which are all connected. The reduced pressure in the rear plenum 301 causes the one way valve 323 to open, closing the switch 329, and energizing the motor 243. As the motor turns and spins the impeller 233 within the impeller chamber 235 (which is now loaded with a dose of medicine powder), air flows into the inhaler 200 from the inflow port 325 through the rear plenum 301, forward through air supply hole 311 into the center plenum 303, through the channels 305 and into the impeller chamber 235, as schematically illustrated in FIGS. 30 and 31. The airflow also prevents powder from flowing into the motor.

The impeller spinning at approximately 14,000 rpm efficiently mixes the powder with the air flowing through the impeller chamber. Referring still to FIGS. 30 and 31, powder-laden air passes out of the impeller chamber 235 through the outflow holes 227 and into the front chamber 219. The sharp edges on the outflow holes 227 facing the impeller chamber substantially prevent a buildup of powder in the holes, to prevent clogging. Outside air enters into the distribution chamber 307 through the front air inlet 231 which may be adjustable or varied in size to increase or decrease air flow for enhanced delivery efficiency. From the distribution chamber 307, the outside air passes radially inwardly through radial holes 229 which restrict flow by design. The outside air is intended to provide a boundary layer for the powder-laden air in the front chamber 219. The powder-laden air surrounded by the boundary layer of outside air is drawn out of the front chamber 219 into the user's mouth, throat and lungs, to deliver the powdered drug. The boundary layer helps to keep powdered drug from accumulating or collecting on the inside walls of the mouthpiece and is also believed to help to prevent the powder from settling out in the users mouth and throat. When the user stops inhaling, the valve 323 closes opening the switch 329 and stopping the motor. The inhaler accordingly is breadth actuated. Since the valve 323 opens with even a slight pressure drop, the inhaler requires only slight inhalation to turn on.

The inhaler 200, like the inhaler shown in FIG. 1, produces a slow moving aerosol mist of fine powder that can be easily and safely inhaled deep into the lungs to maximize the actual delivered dosage and effect of the drug. Unlike many prior inhalers, the present inhaler does not require excessive or deep inhalation to achieve drug delivery. Accordingly, the user's lung function is not nearly so important as in the prior art. The present inhaler is therefore highly advantageous for use by persons with impaired lung function.

In addition, exhalation into the inhaler 200 is prevented as the one way valve 323 closes with only a slight pressure rise in the rear plenum 301. If the user coughs or blows into the inhaler 200, some of the moisture laden breath will exhaust out in part through the front air inlet 231 but will not appreciably reach into the impeller chamber, absent repeated or excessive exhalation into the inhaler.

The present inhaler may include design features provided by the recognition that different powdered drugs have different characteristics. Powdered mixtures of drugs have varying particle sizes and distributions, densities, cohesiveness (the tendency for the drug particles to stick to themselves) and adhesiveness (the tendency for the drug particles to stick to surfaces of the inhaler). Thus, for increased delivery efficiency, the flow parameters of the inhaler should advantageously be adjusted for the specific drug being delivered. These adjustments can be made by adjusting the rotation speed of the impeller 233, and by varying the air flow through the impeller chamber. The air flow through the impeller chamber can be controlled by a slide or dial aperture 327 increasing or decreasing the size of the opening o the air supply hole 311. Alternatively the air supply hole 311 can be punched or drilled out to a specific size dedicated to a specific drug. Consequently, the inhaler is advantageously provided with speed setting or adjusting circuitry for the motor and an air flow control aperture or air supply hole size matched to the characteristics of the drug that the inhaler will deliver.

Electrical wiring in these drawings has not been shown for clarity as such wiring is already known in the prior art. The drawings show the preferred sizes of the features of the inhaler.

While the invention has been described with reference to particular embodiments, those skilled in the art will be able to make various modifications to the described embodiments without departing from the spirit and scope thereof. Those skilled in the art will also appreciate that various features described in connection with one embodiment may be used separately or in combination on either embodiment.

I claim:

1. A dry powder inhaler for mixing air and powdered drug particles comprising: a housing; a mixing chamber in the housing, the mixing chamber having spaced apart front and back walls with the front and back walls forming a generally disk shaped space therebetween; an impeller within the space of the mixing chamber, the impeller occupying at least 80% of said space thereby providing proper mixing mixing of air and powdered drug particles for inhalation by a patient; a motor linked to the impeller; at least one inlet opening leading into the mixing chamber; and at least one outlet opening leading out of the mixing chamber.

2. The dry powder inhaler of claim 1 further comprising two oppositely extending tapering arms on the impeller forming an equilateral parallelogram.

3. The dry powder inhaler of claim 2 further comprising a shaft on the motor extending into the mixing chamber and attached to the impeller, with the arms of the impeller having outer edges extending parallel to the shaft.

4. The dry powder inhaler of claim 1 wherein the mixing chamber has a diameter to width ratio of about 4:1.

5. The dry powder inhaler of claim 1 wherein the mixing chamber is disk shaped and has a uniform cross section.

6. The dry powder inhaler of claim 1 with the mixing chamber including a rear wall having a single opening in it, and with the single opening forming the at least one inlet.

7. The dry powder inhaler of claim 6 further comprising a shaft on the motor extending through the single opening into the mixing chamber and attached to the impeller.

8. The dry powder inhaler of claim 1 further comprising a flat front surface and a flat rear surface on the impeller.

9. The dry powder inhaler of claim 8 with the mixing chamber further comprising a flat rear wall and a flat front wall, with the flat front and rear walls parallel to the flat front and rear surfaces of the impeller.

10. The dry powder inhaler of claim 9 wherein the rear wall is integral with the housing and the front wall is removable from the housing.

11. The dry powder inhaler of claim 1 wherein the impeller has a diameter which is at least 95% of the diameter of the mixing chamber.

12. A method for dry powder inhalation comprising the steps of:

preparing a dry powder drug formulation by attaching active drug particles to diluent particles which are much larger than the active drug particles;

loading the dry powder drug formulation in a mixing chamber of an inhaler;

inhaling on a mouthpiece of the inhaler, with the mixing chamber connecting to the mouthpiece via a flow path;

sensing the inhaling;

switching on a motor in response to the sensed inhalation;

spinning up an impeller in the mixing chamber, linked to the motor;

separating the active drug particles and the diluent particles within the mixing chamber via the spinning impeller; and restricting air flow through the inhaler via throttling apertures to thereby limit inhalation of air and drug and diluent particles out of the inhaler to a clinically negligible velocity.

13. The method of claim 12 wherein the diluent particles are larger than 50 microns diameter.

14. The method of claim 12 wherein the impeller spins at about 12,500 rpm.

15. The method of claim 12 wherein the impeller spins at about 14,000 rpm.

16. A dry powder inhaler comprising:

a housing;

a mixing chamber in the housing, the mixing chamber having a flat rear wall and a flat front wall, with the rear wall integral with the housing and the front wall removable from the housing;

an impeller in the mixing chamber, the impeller having blades without pitch and the blades having flat front and rear surfaces parallel to the flat front and rear walls of the mixing chamber;

a motor linked to the impeller;

at least one inlet opening leading into the mixing chamber; and at least one outlet opening leading out of the mixing chamber.

17. The dry powder inhaler of claim 16 wherein the impeller has a diameter which is at least 95% of the diameter of the mixing chamber.

18. The inhaler of claim 16 wherein the mixing chamber is disk-shaped and the impeller is centered in the mixing chamber.

19. The dry powder inhaler of claim 16 with the mixing chamber including a rear wall having a single opening in it, and with the single opening forming the at least one inlet.

20. The dry powder inhaler of claim 19 further comprising a shaft on the motor extending through the single opening into the mixing chamber and attached to the impeller.

21. A dry powder inhaler comprising:

a housing;

a mixing chamber in the housing;

an impeller in the mixing chamber, the impeller having flat blades without pitch;

a motor having a shaft linked to the impeller;

at least one inlet opening leading into the mixing chamber;

at least one outlet opening leading out of the mixing chamber;

the mixing chamber including a rear wall having a single opening in it, and with the single opening forming the at least one inlet; and the shaft of the motor extending through the single opening into the mixing chamber and attached to the impeller.

* * * * *